United States Patent
Bobbert

(10) Patent No.: US 8,236,357 B2
(45) Date of Patent: Aug. 7, 2012

(54) MILD COMPOSITION FOR SKIN DISINFECTION

(75) Inventor: Ilja Bobbert, Hilversum (NL)

(73) Assignee: Aseptix Research B.V., Hilversum (NL)

( * ) Notice: Subject to any disclaimer, the term of this patent is extended or adjusted under 35 U.S.C. 154(b) by 327 days.

(21) Appl. No.: 12/312,874

(22) PCT Filed: Dec. 12, 2007

(86) PCT No.: PCT/EP2007/063831
§ 371 (c)(1),
(2), (4) Date: Jun. 12, 2009

(87) PCT Pub. No.: WO2008/071746
PCT Pub. Date: Jun. 19, 2008

(65) Prior Publication Data
US 2010/0028458 A1  Feb. 4, 2010

(30) Foreign Application Priority Data
Dec. 13, 2006 (EP) .................... 06126044

(51) Int. Cl.
*A61K 33/40* (2006.01)
(52) U.S. Cl. .................................. 424/616
(58) Field of Classification Search .......... None
See application file for complete search history.

(56) References Cited

U.S. PATENT DOCUMENTS
5,458,881 A  10/1995 Berger et al.
2006/0024339 A1  2/2006 Murad FOREIGN PATENT DOCUMENTS
| EP | 1 221 313 A2 | 7/2002 |
| WO | WO 92/21318 A1 | 12/1992 |
| WO | WO 03/039496 A1 | 5/2003 |
| WO | WO 2005/110090 A1 | 11/2005 |

OTHER PUBLICATIONS

"Protelan ENS: A versatile self-emulsifying base", Author unknown, Zschimmer & Schwarz Italiana S.p.A., (URL: http//www.erwebhosting.it/zsi/repository/Protelan%20ENS%20-%20A%20versatile%20self-emulsifying%20base.pdf>), Apr. 2002, pp. 1-26.

"Protelan VE/K: a new natural ingredient for cosmetic products", Author unknown, Zschimmer & Schwarz Italiana S.p.A., (URL: http//web.archive.org/web/20051104003413/http://www.erwebhosting.it/zsi/repository/Protelan+VE-K+-+a+new+natural+ingredient+for+cosmetic+production.pdf>), Nov. 2005, pp. 1-15.

"Protelan AG 8. A new acylglutamate with outstanding applications," Zschimmer & Schwarz Italiana S.p.A., pp. 1-30, Jan. 2004.

*Primary Examiner* — Robert A Wax
*Assistant Examiner* — Jessica Worsham
(74) *Attorney, Agent, or Firm* — Oliff & Berridge, PLC

(57) ABSTRACT

The present invention discloses compositions for aqueous skin disinfection comprising hydrogen peroxide in a concentration of at least 0.1% to 10% (w/w), preferably 0.2-6%, and an N-acylated amino acid and/or peptide in the range of 0.1-20% (w/w), preferably 0.1-10%, more preferably 0.2-8%, and most preferably 0.2-5% (w/w). The N-acylated amino acid composition may be N-acylated glutamic acid and/or an N-acylated wheat protein hydrolysate, or a salt thereof.

16 Claims, No Drawings

MILD COMPOSITION FOR SKIN DISINFECTION

The present invention relates to mild and highly skin compatible, biocidally active compositions for disinfection, sanitizing, antimicrobial regulation and sebum regulation of the skin.

Human skin is permanently populated with a multitude of different microorganisms (bacteria, yeasts and fungi). The commensal microorganisms living on or in the skin may form part of a microflora that is either resident (normal) or transient. The resident microbial flora, which is essential for good health of the skin, consists mainly of staphylococci (*Staphylococcus epidermis* and *Staphylococcus hominis*), corynebacteria, Gram$^+$ propionibacteria such as *Propionibacterium acnes*, and also a yeast flora mainly composed of *Pityrosporum ovale*. *Pityrosporum ovale* is for example believed to be involved in many skin disorders, such as seborrhoic dermatitis, folliculitis, confluent and reticulate papillomatosis and psoriatic lesions.

Most of the skin bacteria are present on the superficial squamous epidermis, colonizing dead cells, and closely associated with the sebaceous and sweat glands. The excretions from these glands provide water, amino acids, urea, electrolytes and specific fatty acids serving as nutrient elements mainly for *Staphylococcus epidermidis* and certain aerobic corynebacteria.

Skin infections are usually caused by disruption of the ecological equilibrium of the resident flora following colonization of the skin by pathogenic exogenous germs or following abnormal proliferation of an endogenous strain. The pathogenic germs that are the most common are *Pseudomonas aeruginosa* (Gram$^-$), which is responsible for small spots, folliculitis, red patches and pruritus, *Candida albicans*, which can cause inflammation at the labial angle, cutaneous candidiasis, pruritus, folliculitis and aphthae, *Staphylococcus aureus*, which can cause spots, folliculitis, impetigo and furuncles, and Group A Streptococci, responsible for impetigo.

In many industries, infection control and the prevention of spread of disease-causing micro-organisms is a major concern. In veterinary, healthcare, paramedical, hospitality, food processing and industrial applications, the prevention of contamination with and spreading of pathogenic microorganism is of crucial importance. Often, spreading of micro-organisms occurs via the hands. Viruses and bacteria on contaminated hands are easily spread among people in health care facilities such as hospitals. But also in washroom, health & wellness, school and household applications, the maintenance of high hygiene standards is becoming increasingly important.

Washing hands with detergents or soaps is a way to reduce the risk of infection. However, in certain environments, such as hospitals or food processing, the required level of disinfection cannot be achieved by commonly used soaps and detergents. Consequently, hand disinfectants have been developed to achieve higher levels of disinfection where the need exists.

Thus, this recent trend towards higher levels of infection control in hospital settings and in food & hospitality sectors, combined with the increasing awareness for infectious diseases that can be transferred via the skin and respiratory system, have opted the industry to come up with disinfecting compositions that can be used more frequently throughout the day. These compositions must be hypoallergenic, non-toxic and not produce any undesirable residue on the skin.

A problem with existing skin disinfection products, typically containing alcohols, iodines/iodophors, chlorhexidine gluconate (CHG), phenolic compounds, triclosan, quaternary ammonium compounds, or combinations thereof, is that they often sacrifice disinfectant activity for the sake of skin mildness or vice versa. For example, while raising the concentration of the active ingredient may lead to a higher level of disinfection, such higher concentration frequently leads to increased skin irritation, especially when frequently used. Many of the currently available compounds cause skin dryness, skin irritation or are suspect for unwanted side-effects. Many of the known and widely used skin disinfection compounds are under pressure or even banned from certain markets. This has caused the industry to come up with new solutions for this problem.

Object of the invention is to provide a highly efficacious antimicrobial composition with improved skin compatibility and user friendliness. It was found that the combination of hydrogen peroxide and N-acylated amino acids and/or peptides, preferably having an acidic pH, provide for a mild yet highly effective disinfectant composition.

WO92/21318 describes N-acyl derivatives of amino acids derived from cereal protein hydrolysates, salts thereof, and cosmetic and detergent compositions containing said derivatives or their salts.

EP 1 221 313 and WO 03/039496 describe detergent or cosmetic compositions having hydrating and preservative properties and simultaneously anti-dandruff and/or anti-odour properties. The compositions of EP 1 221 313 comprise a salt of undecylenoil glutamate and/or undecylenoil hydrolyzate of wheat and/or rice proteins and the compositions of WO 03/039496 include a capryloyl glutamate salt and/or capryloyl hydrolysate of wheat and/or rice protein. Since such salts are able to perform also a preservative and hydrating effect, the compositions do not need the addition of further preservative or hydrating agents or, at most, contain concentrations thereof which are not efficacious per se. These compositions are not described for disinfecting the skin (i.e. instantly killing pathogenic micro-organisms) and are also not capable of providing sufficient anti-microbial kill in sufficiently short contact times to produce an acceptable skin disinfection composition.

US2006/0024339 provides a method for managing redness of skin associated with a dermatological condition, the method comprising topically administering to the skin of a patient a pharmaceutical composition comprising an extract of goji berries. The pharmaceutical composition used in these methods can further comprise at least one carboxylic acid. Optionally, the composition may contain various other components, among which at least one amino acid or hydrogen peroxide. A useful amino acid may be N-acetylcystein. However, the combination of hydrogen peroxide and N-acetylcystein is not disclosed and no reference is made to the disinfecting or antimicrobial capacity of the compositions.

The use of lauroyl glutamate in an Emulsifying Natural System (Protelan ENS) has been disclosed in a brochure of Protelan ENS (Zschimmer & Schwarz Italiana S.p.A.). Protelan ENS is a blend of glyceryl stearate, cetearyl alcohol, stearic acid and sodium lauroyl glutamate. In a series of stability and compatibility tests, an emulsion comprising 5% hydrogen peroxide in the water phase and 20% Protelan ENS in the oil phase was shown to provide a stable cream.

None of the prior art describes the high disinfection power of compositions as described herein. It was found that hydrogen peroxide and N-acylated amino acids separately have low disinfection power, even in relatively high concentrations. Only after combining hydrogen peroxide and N-acylated amino acids in an aqueous system, a surprising synergistic effect comes to effect. The synergy is highly significant and is totally unexpected when looking at the performance of the two ingredients separately.

Thus, the present invention provides a composition for disinfecting skin comprising hydrogen peroxide in the range of 0.1-10% (w/w), preferably 0.2-6%, and an N-acylated amino acid and/or peptide in the range of 0.1-20% (w/w), preferably 0.1-10%, more preferably 0.2-8%, and most preferably 0.2-5% (w/w).

The term "N-acylated amino acid and/or peptide" according to the invention refers to peptides and/or free amino acids, or salts thereof, wherein at least 50% of the amino groups of the free amino acids and/or of the peptides, is acylated. Preferably, all the amino groups are acylated. The amino acid may be a single amino acid or may be a mixture of amino acids obtainable by hydrolysis of a suitable protein substrate. In the latter case, short peptides may be present, typically comprising peptides with an average molecular weight lower than about 4000 Dalton, preferably lower than about 2000 Dalton.

The N-acylated peptide and/or N-acylated amino acid to be used according to the invention preferably has a structure according to Formula I as follows:

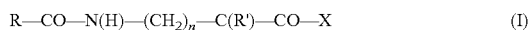

R—CO—N(H)—(CH$_2$)$_n$—C(R')—CO—X    (I)

or a salt thereof,
wherein R—CO— represents an acyl group wherein R is a saturated or unsaturated, straight of branched C5 to C21 radical,
n is 0, 1 or 2,
R' represents an amino acid side chain, and
X is OH or a group according to Formula II:

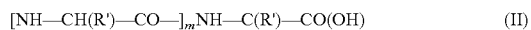

[NH—CH(R')—CO—]$_m$NH—C(R')—CO(OH)    (II)

wherein m ranges from 0 to such a value that the compound of Formula II specifies a peptide having an average molecular weight of about 100 to about 3900 Dalton, preferably of about 100 to about 1900 Dalton, more preferably about 100 to about 1300, most preferably about 100 to about 700 Dalton.

Suitable salts are those wherein the dissociated carboxylic groups are neutralised with cations belonging to the group of alkaline metals and alkaline earth metals, ammonia, other metals such as lead, iron, aluminum, manganese, copper, zinc, or by organic bases such as arginine, lysine, mono-, di-, or triethanolamine, ornithine, histidine, morpholine, or choline. Such neutralising cations can be utilised also in combinations with one another.

Preferably, the R moiety of the acyl group is a C6 to C20 radical. More preferred are the straight chain variants thereof (saturated as well as unsaturated). Especially preferred acyl groups are octanoyl (capryloyl), nonanoyl, decanoyl, undecanoyl, undecylenoyl, dodecanoyl (lauroyl), tridecanoyl, tetradecanoyl (myristyl), hexadecanoyl (palmitoyl), octadecanoyl (stearoyl), oleoyl, and mixtures thereof.

When X is OH, the compound of Formula I represents an amino acid. According to the invention, the term "amino acid" may refer to an alpha-, beta- or gamma-amino acid, i.e. n is 0, 1 or 2, but preferably is an alpha-amino acid (n is 0).

R' represents an amino acid side chain occurring in natural proteogenic amino acids, or a side chain that is modified as compared to those occurring in natural proteogenic amino acids by substitution of a hydrogen atom in the side chain for a hydroxyl, methyl, ethyl or other suitable group.

A proteogenic amino acid is an amino acid that is encoded by DNA. An example of a modified amino acid is hydroxyproline, occurring for instance in collagen.

Preferred amino acid precursors for the N-acylated compounds of Formula I wherein X is OH are chosen from the group of polar amino acids, such as glutamic acid, aspartic acid, glutamine, asparagine, lysine, arginine, histidine, proline, threonine, serine. Especially preferred amino acids are glutamic acid, aspartic acid, lysine.

When X is a compound of Formula II, X represents an amino acid unit when m is 0 or a peptide when m is $\geq 1$. The value of m may typically range from 1 to 18 for x to specify a peptide with a molecular weight from about 200 to about 1900 Dalton.

Preferred peptide and/or amino acid precursors for the N-acylated compounds of Formula I are protein hydrolysates. Protein hydrolysates are degradation products of protein substrates, and typically are obtained by acidic, alkaline and/or enzymatic hydrolysis of a protein substrate, thereafter having an average molecular weight of 100 to 2000, preferably 100 to 1400 and more particularly 100 to 800. Most preferably, the protein substrate is predominantly hydrolysed to the individual constituting amino acids, preferably wherein the individual amino acids constitute at least 50% (w/w) of the protein hydrolysate.

Suitable protein substrates for example are vegetable proteins, like wheat, rice, soya, sunflower, maize, pea, almond and potato protein; animal proteins, like milk, gelatin, collagen, keratin protein; microbial proteins, like algal, yeast of fungal protein.

Protein substrates may be chosen based on their amino acid composition. Preferably, the protein substrate has a high level of glutamic acid/glutamine residues, leading to a protein hydrolysate with a high glutamic acid content. An example of such a preferred protein substrate is wheat protein.

The compounds according to Formula I are conveniently obtained by N-acylation of the amino acid and/or peptide precursors as described above, using carboxylic activated derivatives of the fatty acid of formula RCOOH, R being defined as above, by standard methods known in the art. Such derivatives are for example the symmetric anhydrides of these acids or acid halides.

N-acylated amino acids and their salts that may be mentioned, for example, are those of N-acylglutamate, such as monosodium cocoylglutamate, monosodium lauroylglutamate, disodium C14-C20 alkylglutamate, the C14-C20 alkyl radical being derived from hydrogenated tallow, sold respectively under the names "Acylglutamate CS-11", "Acylglutamate LS-11" and "Acylglutamate HS-21" by Ajinomoto. Examples of acylglutamates also include sodium cocoylglutamate and sodium laurylglutamate sold by Clariant under the Hostapon CCG/CLG/KCG trade names and Protelan AG 8 (capryloylglutamate) and Protelan AGL 95 (sodium lauroylglutamate) and Protelan AGL 5/C (sodium cocoylglutamate) of Zschimmer & Schwarz.

Mention may also be made of N-acyl lysines such as lauroyllysine sold under the name "Amihope LL" by Ajinomoto.

Among the N-acylated hydrolysed proteins that may be mentioned are those derived from all or part of collagen or keratin, such as sodium lauroyl collagen and palmitoyl keratin sold under the names "Proteol B 30" and "Lipacide PK" by the company SEPPIC, or from wheat, such as potassium undecylenoyl hydrolysed wheat protein sold as "Protelan AG 11" by Zschimmer & Schwarz.

The compositions as described herein may contain mixtures of two or more of the N-acylated products mentioned above.

The compositions as described herein preferably has a pH in the range of 2 to 6, more preferably 3 to 6, most preferably 3.5 to 5.

The compositions as described herein may further comprise a surfactant, such as an amphoteric, an anionic, a cationic and/or a non-ionic surfactant.

Suitable amphoteric surfactants include amphoteric alkyl polyglucosides, alkyl betaines, alkyl amidopropyl betaines, alkyl amidopropyl betaine amides, alkyl sulfobetaines, amine oxides, amphocarboxyacetates, amphocarboxydiacetates, amphocarboxypropionates, amphocarboxydipropionates, and/or derivates thereof.

Suitable anionic surfactants include alkylsulphates, alkylethersulphates, amido/amidoethersulphates, alkylsemisulphosuccinates, alkylsulphosuccinates, alkylethersemisulphosuccinates, alkylethersulphosuccinates, acylamidosemisulphosuccinates, acylamidosulphosuccinates, dodecylbenzenesulphonic acid, alkyl/alkylethersulphoacetates, salts of sulphonated and/or sulphated organic molecules (for example, alpha-olefin sulphonates), alkyl/alkylether carboxylates, alkylphosphonates, esters of phosphoric acid, acyl isothionates, and salts thereof. Preferred anionic surfactants may be chosen from phosphoric acid esters, alkylphosphonates, alkylsuphates, alkylethersulphates, alkylsulphosuccinates, alkylethersulphosuccinates, as a potassium, sodium, ammonium, zinc, aluminium or triethanolamine salt. Even more preferred are the zinc or aluminum salt forms.

Suitable cationic surfactant include skin conditioning cationic polymers, preferably from the polyquarternium-type surfactants, such as comprising MethacrylAmidoPropyl Trimethyl Ammonium Chloride, DiAllyl DiMethyl Ammonium Chloride or MethAcryloyloxyethyl Trimethyl Ammonium MethylSulfate groups.

Suitable non-ionic surfactants include amides, ethoxylated and non-ethoxylated fatty amines, ethoxylated nonylphenols, APGs (alkylpolyglucosides), AEGs (alkylethoxyglucosides), esters/ethers of fatty acids with glycerol and/or ethoxylated and non-ethoxylated sugars, ethoxylated/propoxylated and non-ethoxylated/propoxylated esters, ethoxylated/propoxylated and non-ethoxylated/propoxylated fatty alcohols.

The compositions as described herein further may contain a carboxylic acid or a salt thereof, the carboxylic acid preferably selected from the group of citric acid, glycolic acid, lactic acid, benzoic acid, salicylic acid and 2-furan carboxylic acid.

The compositions as described herein further may contain the usual ingredients for compositions for use on the skin. For instance, the composition may include skin emollients, stabilizers, pearlizing agents, thickening agents, preservatives, coloring agents or dyes and perfumes.

Emollients may include glycerol, glycerides, polyglycerol, aloe vera, vitamin E, sorbitol, allantoin, cationics, polymers, castor oil, lanolin and its derivatives and cetyl alcohol.

The composition may be thickened via the methods known to the man skilled in the art, for example by addition of Sodium Chloride or a combination of Sodium Chloride and specific types of surfactants (such as Sodium Lauryl Ether Sulfate or Betaines), or by addition of (hydroxy)cellulose based or (cross-) polymer based thickening agents. Preferably, the composition is thickened by the use of (hydroxy) cellulose based or polymer based thickening agents, such as Klucel types (Hercules Chemicals), Natrosol types (Hercules Chemicals), Carbopol types (Noveon), or Oxetal VD 92 of Zschimmer & Schwarz. Via these methods, and adjustment of pH range, a whole range of viscosity levels may be achieved.

The composition of the present invention may be preserved by the use of preservatives which are compatible with hydrogen peroxide, such as various types of parabens, benzyl alcohol, benzoic acid, potassium benzoate, salicylic acid, potassium salicylate, etc.

The composition of the present invention may also comprise a sequestering agent, such as a cation sequestering agent chosen from ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), and salts thereof or more preferably is chosen from acetanilide, trisodium ethylenediamine disuccinate, phosphonic acid derivatives having 1 to 5 phosphonic acid groups, for instance a Dequest phosphonate (Solutia), 1-hydroxyethylidene-1,1-diphosphonic acid (HEDP), amino tri(methylene phosphonic acid), diethylenetriamine-penta(methylene phosphonic acid), 2-hydroxy ethylimino bis(methylene phosphonic acid), and ethylene diamine tetra(methylene phosphonic acid).

The compositions as described herein may be in the form of an aqueous solution or an emulsion, such as a lotion, a foam, a liquid soap, a spray, a gel, a cream, and the like, or in the form of an impregnated wipe. When the composition comprises an oil phase and a water phase, the composition does not contain the self-emulsifying base Protelan ENS in a concentration of 20% (w/w).

In one embodiment, the composition is an aqueous solution, which can have a varying degree of viscosity.

In a preferred embodiment, the composition is applied as a foam in order to increase contact surface and contact time and avoid spilling or dripping of the required dose off the hands, as may be the case when using a spray formulation. The use of the N-acylated amino acid in the compositions as described herein already provides foaming capacity to the composition.

Advantageously, the compositions as described herein are able to provide adequate levels of disinfection while not being irritating to the skin or mucous membranes. The compositions are non-irritating due to the inclusion of highly skin compatible N-acylated amino acids/protein hydrolysates, mild surfactant package and low concentrations of other mild additives, which may be employed as described above. The composition has broad-spectrum activity, the degree of which is unexpected given the germicidal activity of the individual ingredients. In particular, the composition has bactericidal, fungicidal and virucidal activity. A synergy exists amongst the ingredients of the present compositions such that an effective disinfectant is provided that is highly suitable for use on skin.

Thus, the compositions as described herein are advantageously used for all applications where disinfection of the skin or mucous membranes may play a role. The compositions may be used as an antimicrobial composition for daily use, such as in a hand soap, an antimicrobial shower gel, an impregnated wipe, or for intimate hygiene solutions. The compositions may be used for preventing, regulating or curing microbial-originating skin disorders or infections, such as, but not limited to, acne, seborrhoic dermatitis, folliculitis, confluent and reticulate papillomatosis and psoriatic lesions, and athlete's foot.

EXAMPLES

Several biocidal skin compositions were prepared according to the present invention and compared to biocidal skin compositions as known in the art, such as combinations of hydrogen peroxide and betaines. The compositions were prepared in distilled water using commercially available concentrated stocks of the various components.

Explanation of the Products Used

| | |
|---|---|
| Protelan AG 8 | Disodium Capryloyl Glutamate (Zschimmer & Schwarz) |
| Protelan AG 11 | Potassium Undecylenoyl Hydrolyzed Wheat Protein (Zschimmer & Schwarz) |
| Protelan AGL 95 | Sodium Lauroyl Glutamate (Zschimmer & Schwarz) |
| Monafax 1214 | Aliphatic Phosphoric Acid Ester (Uniqema) |
| Texapon NSO | Sodium Lauryl Ether Sulfate (Cognis) |
| Zetesol NL U | Sodium Lauryl Ether Sulfate (Zschimmer & Schwarz) |
| Zetesol Zn | Zinc Coceth Sulfate (Zschimmer & Schwarz) |
| Tego Betaine F | Cocamidopropyl Betaine (Degussa) |
| Mackam CB 818 | Cocamidopropyl Betaine (McIntyre) |
| Octaquest | Trisodium Ethylenediamine Disuccinate |

Biocidal activity of the compositions was tested using a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements). One ml of a test suspension containing about $10^8$ cfu of the test microorganism per ml is added to 8 ml of the composition to be tested, and 1 ml milli-Q water is added. A clean and dirty condition is simulated by adding bovine albumin serum (0.3% and 3.0% respectively). After 1, 3 and 5 minutes contact time, the amount of viable bacteria was determined. The EN 1276 norm prescribes a log 5 reduction in viable cell count after a contact time of 5 minutes.

The results are shown in Tables 1 to 3.

TABLE 1

| | Composition | | | | | | | | |
|---|---|---|---|---|---|---|---|---|---|
| | 1 | 2 | 3 | 4 | 5 | 6 | 7 | 8 | 9 |
| Components | | | | | | | | | |
| Hydrogen Peroxide | 3% | 3% | 3% | 3% | 3% | 3% | 3% | 3% | 3% |
| Protelan AG 8 | 1.95% | | 1.95% | 1.95% | | | 1.95% | 1.95% | |
| Protelan AGL 95 | | | | | | | | | 1.95% |
| Protelan AG 11 | | 0.72% | | 0.72% | | | | 0.72% | |
| Tego Betain F50 | 1.52% | 1.52% | | | 1.52% | 1.52% | 1.52% | 1.52% | 1.52% |
| Zetesol Zn | | | 1.25% | 1.25% | 1.25% | | | | |
| Monafax 1214 | | | | | | | 0.8% | | |
| pH (lactic acid) | 4 | 4 | 4 | 4 | 4 | 4 | 4 | 4 | 4 |
| Log reduction | | | | | | | | | |
| *S. aureus* | | | | | | | | | |
| 3 min. | >6.6 | 4 | >6.6 | >6.6 | 2.2 | 1 | >6.6 | >6.6 | 5.2 |
| 5 min. | >6.6 | 5 | >6.6 | >6.6 | 4 | 3 | >6.6 | >6.6 | >6.6 |
| *S. thyphimurium* | | | | | | | | | |
| 3 min | >6 | 4 | >6 | >6 | 1 | nc* | >6 | >6 | 4.6 |
| *E. coli* | | | | | | | | | |
| 3 min. | >6 | 4.6 | >6 | >6 | 3 | 2 | >6 | >6 | 4.8 |

*nc = not countable

TABLE 2

| | Composition | | | | | | | |
|---|---|---|---|---|---|---|---|---|
| | 10 | 11 | 12 | 13 | 14 | 15 | 16 | 17 |
| Components | | | | | | | | |
| Hydrogen Peroxide | 2.5% | 2.5% | 2.5% | 2.5% | 2.5% | 2.5% | 2.5% | 2.75% |
| Protelan AG 8 | 1.95% | 1.95% | 1.95% | 1.95% | 1.95% | 1.95% | 1.95% | 1.95% |
| Protelan AG 11 | | | | 0.72% | 0.72% | | 0.72% | |
| Tego Retain F50 | 1.9% | 1.9% | 1.9% | 1.9% | | 1.9% | 1.9% | 1.9% |
| Zetesol Zn | | 2.5% | 1% | 1% | | 1% | 1% | 2.25% |
| Texapon NSO | | 0.84% | | | | | | 1.12% |
| Monafax 1214 | | | | | | 0.64% | 0.64% | 0.64% |
| EDTA | | | | | | | 0.1% | 0.15% |
| Octaquest | 0.05% | | | | | 0.05% | | |
| Na-benzoate | | | 0.15% | 0.15% | | | | 0.15% |
| Na-salicylate | | | | 0.1% | | | | 0.1% |
| Furan Carboxylic Acid | | 0.05% | | | | | | |
| NaCl | | | | | 1% | | | |
| pH (citric acid) | 4 | 4 | 4 | 4.5 | 4 | 4 | 4.5 | 5.5 |
| Log reduction | | | | | | | | |
| *S. aureus* | | | | | | | | |
| 3 min. | 4.4 | 5.4 | >6.6 | 5.6 | 4.8 | 5.6 | >6.6 | >6.6 |
| 5 min. | >6.6 | >6.6 | >6.6 | >6.6 | >6.6 | >6.6 | >6.6 | >6.6 |

TABLE 3

| Components | Composition 18 | 19 | 20 | 21 | 22 | 23 | 24 | 25 |
|---|---|---|---|---|---|---|---|---|
| Hydrogen Peroxide | 2% | 2.5% | 2.5% | 2.5% | 2% | 2% | 2% | 2% |
| Protelan AG 8 | 2.35% | 1.95% | 1.95% | 1.95% | | 3.12% | 1.95% | 3.12% |
| Mackam CB 818 | 1% | 2% | 1.9% | 1.9% | 1.9% | 1.9% | | 1.9% |
| Zetesol NL U | 3.35% | 3.35% | 4.20% | 4.20% | 3.35% | 3.35% | 3.35% | 3.35% |
| Glycerine | 1% | 1% | 2% | 2% | 1% | 1% | 1% | 1% |
| Na-benzoate | | | 0.15% | 0.15% | | | | |
| Na-salicylate | | 0.1% | | 0.1% | | | | |
| pH (lactic acid) | 4 | 4 | 3.5 | 3.5 | 4 | 4 | 4 | 4.5 |
| Log reduction | | | | | | | | |
| E. coli 1 min. | >5 | >5 | >5 | >5 | 1.1 | >6 | >6 | >6 |
| S. aureus 1 min. | >5 | >5 | >5 | >5 | 2.3 | >6 | >6 | >5 |

Compositions 1 to 4, 7 to 21 and 23 to 25 are compositions according to the present invention. These compositions show high antimicrobial efficacy, especially where the composition is further completed with an anionic or amphoteric surfactant. The compositions 18 to 21 even passed the norm (>log 5 reduction) on all test organisms *Escherichia coli, Pseudomonas aeruginosa, Staphylococcus aureus*, and *Enterococcus hirae* within only 1 minute contact time, in both simulated clean and dirty conditions.

Compositions 5, 6 and 22 are compositions which are not according to this invention and show substantially less or no antimicrobial activity. These examples clearly show that hydrogen peroxide itself does not have sufficient disinfection capacity and that the compositions containing hydrogen peroxide and an N-acylated amino acid are, surprisingly, highly effective.

In order to further evidence the influence of other surfactants in the compositions, composition 3, 4 and 24 were prepared. These compositions do not contain cocamidopropyl betaine, a surfactant with slight biocidal characteristics, and were shown to pass the EN 1276 norm. A comparison of compositions 22 and 24 further evidences that the influence of cocamidopropyl betaine on the efficacy of the composition is not present indeed.

The compositions 18 to 21 also pass the European norm for hygienic hand washing, EN 1499 with only 30 seconds contact time. A composition without either hydrogen peroxide or the N-acylated amino acid failed the test, even with a contact time of 60 seconds.

Surprisingly, the compositions as described herein have also virucidal efficacy. Compositions 18 to 21 have shown to kill enveloped blood borne viruses on model viruses bovine viral diarrhea virus (BVDV) and vaccinia virus in a controlled virucidal suspension test with a contact time of only 30 seconds. Efficacy against both BVDV and vaccinia provides, under accepted German standards (Robert Koch Institute, Deutsche Gesellschaft Für Hygien und Medizin), for an effect against all enveloped blood borne viruses, such as HIV, HCV, HBV, Human Influenza, H5N1 and SARS (tested at Mikrolab GmbH, Dr J. Steinmann).

Compositions 18 to 21 have been tested in a controlled dermatological skin patch test for 48 hours and 72 hours on 50 persons with different skin conditions: 25 with normal healthy skin, 5 with eczema, 1 with allergic skin, and 19 with sensitive skin. The compositions 18 to 21 have been compared to a 1% dilution of Sodium Dodecyl Sulfate (SDS) in water and were scored on erythema, fissure, and scaling. The SDS solution showed clear irritation in 12 cases. With the compositions 18 to 21, after both 48 hours and 72 hours, none of the subjects showed any redness or irritation of the skin. These test results clearly evidence that the broad spectrum and highly bactericidal compositions 18 to 21 were surprisingly mild to the skin.

Important to notice is that bactericidal activity is not the only important variable in the biocidal skin compositions as described herein. It was also found that the compositions are extremely skin friendly and leave the user with a soft and well-cared afterfeel. Skin feel, dirt and sebum removal, lathering effect, moisturisation of the skin, non-stickiness and skin afterfeel should all be considered, together with the bactericidal effect, to arrive at an efficacious composition.

The invention claimed is:

1. A composition for skin or mucous membrane disinfection comprising hydrogen peroxide in a concentration of 0.1% to 10% (w/w), and an N-acylated amino acid and/or peptide, or a salt thereof, in a concentration of 0.1% to 20% (w/w), wherein the N-acylated amino acid and/or peptide comprises an acyl radical having from 5 to 21 carbon atoms;
  wherein when the composition comprises an oil phase and a water phase the composition does not contain a self-emulsifying base of a blend of glyceryl stearate, cetearyl alcohol, stearic acid and sodium lauroyl glutamate.

2. The composition of claim 1, wherein the composition is an aqueous solution.

3. The composition of claim 1, wherein the composition has a pH in the range of 2 to 6.

4. The composition of claim 1, wherein the N-acylated amino acid and/or peptide is an N-acylated polar amino acid.

5. The composition of claim 1, wherein the N-acylated amino acid and/or peptide is an N-acylated wheat protein hydrolysate.

6. The composition of claim 1, further comprising an amphoteric, anionic, cationic, and/or non-ionic surfactant.

7. The composition of claim 6, wherein the amphoteric surfactant is selected from the group consisting of amphoteric alkyl polyglucosides, alkyl betaines, alkyl amidopropyl betaines, alkyl amidopropyl betaine amides, alkyl sulfobetaines, amine oxides, amphocarboxyacetates, amphocarboxydiacetates, amphocarboxypropionates, amphocarboxydipropionates, and derivates thereof.

8. The composition of claim 6, wherein the anionic surfactant is selected from the group consisting of alkylsulphates, alkylethersulphates, amido/amidoethersulphates, alkylsemisulphosuccinates, alkylsulphosuccinates, alkylethersemisulphosuccinates, alkylethersulphosuccinates, acylamidosemisulphosuccinates, acylamidosulphosuccinates, dodecylbenzenesulphonic acid, alkyl/alkylethersulphoacetates, salts of sulphonated and/or sulphated organic molecules, alkyl/alkylether carboxylates, alkylphosphonates, esters of phosphoric acid, acyl isothionates, and salts thereof.

9. The composition of claim 6, wherein the cationic surfactant is selected from skin conditioning cationic polymers.

10. The composition of claim 6, wherein the nonionic surfactant is selected from the group consisting of amides, ethoxylated and non-ethoxylated fatty amines, ethoxylated nonylphenols, APGs (alkylpolyglucosides), AEGs (alkylethoxyglucosides), esters/ethers of fatty acids with glycerol and/or ethoxylated and non-ethoxylated sugars, ethoxylated/propoxylated and non-ethoxylated/propoxylated esters, ethoxylated/propoxylated, and non-ethoxylated/propoxylated fatty alcohols.

11. The composition of claim 1, further comprising a carboxylic acid or a salt thereof, the carboxylic acid being selected from the group consisting of citric acid, glycolic acid, lactic acid, benzoic acid, salicylic acid, and 2-furan carboxylic acid.

12. The composition of claim 1, further comprising a skin emollient selected from the group consisting of glycerol, glycerides, polyglycerol, aloe vera, vitamin E, sorbitol, allantoin, cationics, polymers, castor oil, lanolin and its derivatives, and cetyl alcohol.

13. The composition of claim 1, further comprising stabilizers, pearlizing agents, thickening agents, preservatives, coloring agents or dyes, and perfumes.

14. A method of disinfecting skin or mucous membranes comprising applying the composition of claim 1 to infected skin or mucous membranes.

15. A method of treating skin comprising applying to skin the composition of claim 1 as an antimicrobial composition for daily use.

16. A method for regulating or curing skin infections or skin disorders comprising applying the composition of claim 1 to skin.

* * * * *